US009292742B2

(12) United States Patent
Mukousaka et al.

(10) Patent No.: US 9,292,742 B2
(45) Date of Patent: Mar. 22, 2016

(54) 2D AND 3D ION INTENSITY IMAGE GENERATING APPARATUS, METHOD, AND COMPUTER READABLE STORAGE MEDIUM

(75) Inventors: Shinichi Mukousaka, Tokyo (JP); Kanae Teramoto, Tokyo (JP); Hideki Koike, Tokyo (JP)

(73) Assignees: The University of Electro-Communications, Tokyo (JP); JEOL Ltd., Tokyo (JP)

( * ) Notice: Subject to any disclaimer, the term of this patent is extended or adjusted under 35 U.S.C. 154(b) by 563 days.

(21) Appl. No.: 13/591,462

(22) Filed: Aug. 22, 2012

(65) Prior Publication Data

US 2013/0051608 A1 Feb. 28, 2013

(30) Foreign Application Priority Data

Aug. 24, 2011 (JP) .................. 2011-182459

(51) Int. Cl.
*G06K 9/00* (2006.01)
*G06F 19/16* (2011.01)
*G06F 19/26* (2011.01)

(52) U.S. Cl.
CPC .......... *G06K 9/00523* (2013.01); *G06K 9/0055* (2013.01); *G06F 19/16* (2013.01); *G06F 19/26* (2013.01)

(58) Field of Classification Search
CPC ................. G06F 19/16; G06F 19/26
See application file for complete search history.

(56) References Cited

FOREIGN PATENT DOCUMENTS

JP 2004219140 A 8/2004

OTHER PUBLICATIONS

Neubert et al., "Label-Free Detection of Differential Protein Expression by LC/MALDI Mass Spectrometry", Apr. 16, 2008, American Chemical Society, Journal of Proteome Research, 2008, 7 (6), p. 2270-2279.*
Falkenhagen et al., "Characterization of silsesquioxanes by sizeexclusion chromatography and matrix-assisted laser desorption/ionization time-of-flight mass spectrometry", Jan. 3, 2003, John Wiley & Sons, Rapid Communications in Mass Spectrometry, vol. 17, iss. 4, p. 285-290.*
Schiller et al., "MALDI-TOF MS in lipidomics", Jan. 1, 2007, Frontiers in Bioscience, vol. 12 p. 2568-2579.*
Strohalm et al., "mMass 3.12 User's Guide", Jul. 14, 2011, www.mmass.org, p. 1-74.*
Evisa , "Instrument Database: Bruker Daltonics—ultraflex II & ultraflex II TOF/TOF", 2010, <http://www.speciation.net/Database/Instruments/Bruker-Daltonics/ultraflex-II-amp-ultraflex-11-TOFTOF-;i1499>.*

* cited by examiner

*Primary Examiner* — Stephen R Koziol
*Assistant Examiner* — Timothy Choi
(74) *Attorney, Agent, or Firm* — The Webb Law Firm

(57) ABSTRACT

An image generating apparatus capable of facilitating analysis of a substance having a repeating structure has: an ion intensity data acquisition portion for acquiring ion intensity data arising from the substance, the data including information about a relative intensity of each ion against mass-to-charge ratio; a mass information acquisition portion for acquiring mass information about the repeating unit of the substance; a data alignment portion for aligning the ion intensity data within each given range of mass-to-charge ratios based on the mass information about the repeating unit of the substance; and an image generation portion for generating an image based on the aligned ion intensity data.

13 Claims, 12 Drawing Sheets

| LABEL | END GROUP | REPEAT | ADDUCT | FORMULA |
|---|---|---|---|---|
| A (0) | $C_3H_6O_3$ | $CH_2$ | Na | $C_3H_6O_3[CH_2]_nNa$ |
| A (1) | $C_3H_4O_3$ | $CH_2$ | Na | $C_3H_4O_3[CH_2]_nNa$ |
| A (2) | $C_3H_2O_3$ | $CH_2$ | Na | $C_3H_2O_3[CH_2]_nNa$ |
| A (3) | $C_3H_3$ | $CH_2$ | Na | $C_3O_3[CH_2]_nNa$ |
| A (4) | $C_4H_3$ | $CH_2$ | Na | $C_4O_3[CH_2]_nNa$ |
| A (5) | $C_5H_3$ | $CH_2$ | Na | $C_5O_3[CH_2]_nNa$ |
| B (1) | $C_3H_4O_4$ | $CH_2$ | Na | $C_3H_4O_4[CH_2]_nNa$ |
| B (2) | $C_3H_2O_4$ | $CH_2$ | Na | $C_3H_2O_4[CH_2]_nNa$ |
| B (3) | $C_4O_4$ | $CH_2$ | Na | $C_3O_4[CH_2]_nNa$ |
| B (4) | $C_4O_4$ | $CH_2$ | Na | $C_4O_4[CH_2]_nNa$ |
| B (5) | $C_5O_4$ | $CH_2$ | Na | $C_5O_4[CH_2]_nNa$ |

*FIG. 9*

2D AND 3D ION INTENSITY IMAGE GENERATING APPARATUS, METHOD, AND COMPUTER READABLE STORAGE MEDIUM

BACKGROUND OF THE INVENTION

1. Field of the Invention

The present invention relates to an image generating apparatus, image generation method, and a non-transitory computer readable storage medium.

2. Description of Related Art

In recent years, in order to analyze mass spectra obtained as a result of mass analyses, various methods and apparatus have been developed as well as software products utilizing such methods (see, for example, JP-A-2004-219140). Generally, a mass spectrum is represented as a two-dimensional chart in which mass-to-charge ratio (m/z; where m is a molecular mass and z is a charge number) is plotted on the horizontal axis and ion intensity (relative intensity) is plotted on the vertical axis.

Generally, a lipid is an ester of an aliphatic acid and an alcohol and has a structure in which $CH_2$ repeats itself. Furthermore, a polymer is obtained by polymerization of monomers and has a monomer-repeating structure. Polymerix is known and available from Sierra Analytics, Inc. as a software product for analyzing a mass spectrum of a substance having such a repeating structure. Polymerix has a function of counting the number of spaces between ion peaks in order to estimate the mass of a monomer from a mass spectrum of a polymer.

This function makes it possible to estimate the masses of monomers constituting an unknown polymer but it is impossible to estimate terminal groups and chemical modifications of polymers. In analysis of a lipid, the repeating structure of $CH_2$ is already known, and it is impossible to estimate terminal groups and chemical modifications. That is, with a technique of counting the number of spaces between ion peaks, it is impossible to obtain information about terminal groups and modifications of a substance having a repeating structure from a mass spectrum.

In this way, in the past, it has been difficult to analyze terminal groups and chemical modifications that are important for physical properties of a substance having a repeating structure from a mass spectrum.

SUMMARY OF THE INVENTION

In view of the foregoing problem, the present invention has been made. According to some embodiments of the present invention, image generating apparatus, image generation method, and computer program capable of facilitating analysis of a substance having a repeating structure can be offered.

(1) An image generating apparatus associated with the present invention generates an image for analyzing a substance having a repeating structure and includes: an ion intensity data acquisition portion for acquiring ion intensity data arising from the substance, the data including information about a relative intensity of each ion against mass-to-charge ratio; a mass information acquisition portion for acquiring mass information about the repeating unit of the substance; a data alignment portion for aligning the ion intensity data within each given range of mass-to-charge ratios based on the mass information about the repeating unit of the substance; and an image generation portion for generating the image based on the aligned ion intensity data.

According to this image generating apparatus, an image can be obtained in which ion intensities are expanded not only along the m/z axis but also along the axis of the periodicity of the repeating structure. Consequently, information associated with a physical property (e.g., information about terminal groups or a chemical modification) of the substance having the repeating structure can be confirmed more easily than the conventional mass spectral representation. Accordingly, analysis of a substance having a repeating structure can be facilitated.

(2) In one feature of the image generating apparatus, the data alignment portion may align the ion intensity data along a first axis within each given range of mass-to-charge ratios to form unit data strings and align the unit data strings along a second axis intersecting with the first axis.

According to this image generating apparatus, an image can be obtained in which ion intensities are expanded not only along the m/z axis but also along the axis of the periodicity of the repeating structure. Therefore, analysis of a substance having a repeating structure can be facilitated.

(3) In another feature of the image generating apparatus, the image generation portion may generate a two-dimensional image in which the first axis is taken as an X-axis, the second axis is taken as a Y-axis, and the ion intensities indicated by the ion intensity data are represented as color shades.

According to this image generating apparatus, it is possible to generate an image that makes it easy to check information about deviations of ion peaks, period of ion peaks, and spacing between ion peaks.

(4) In a further feature of the image generating apparatus, the image generation portion generates a three-dimensional image in which the first axis is taken as an X-axis, the second axis is taken as a Y-axis, and the ion intensities indicated by the ion intensity data are plotted on a Z-axis.

This image generating apparatus can create an image which permits one to easily grasp the intensity distribution of ion peaks (distribution variations) or other information.

(5) In a yet other feature of the image generating apparatus, there are further provided: a position-specifying portion permitting one to specify positions in the image created by the image generation portion; and a length-measuring portion for measuring the distance between two points taken along the X-axis, the two points being specified by the position-specifying portion.

According to this image generating apparatus, the difference in mass-to-charge ratio between ion peaks can be easily checked. Accordingly, terminal groups or chemical modifications can be analyzed easily.

(6) An image generation method associated with the present invention is adapted to generate an image used for analysis of a substance having a repeating structure. This image generation method starts with acquiring ion intensity data about the substance, the data including information about a relative intensity of each ion against mass-to-charge ratio. Then, mass information about a repeating unit of the substance is acquired. The ion intensity data are aligned within each given range of mass-to-charge ratios based on the mass information about the repeating unit of the substance. The image is generated based on the aligned ion intensity data.

According to this image generation method, it is possible to obtain an image in which ion intensities are expanded not only along the m/z axis but also along the axis of the periodicity of the repeating structure. Consequently, information related to a physical property such as information about terminal groups and chemical modifications of the substance having the repeating structure can be checked more easily than where the conventional mass representation is used. This can ease analysis of the substance having the repeating structure.

(7) A computer program associated with the present invention is adapted to generate an image used to analyze a substance having a repeating structure, the computer program operating to cause a computer to function as: an ion intensity data acquisition portion for acquiring ion intensity data arising from the substance, the data including information about a relative intensity of each ion against mass-to-charge ratio; a mass information acquisition portion for acquiring mass information about the repeating unit of the substance; a data alignment portion for aligning the ion intensity data within each given range of mass-to-charge ratios based on the mass information about the repeating unit of the substance; and an image generation portion for generating the image based on the aligned ion intensity data.

According to this computer program, an image can be obtained in which ion intensities are expanded not only along the m/z axis but also along the axis of periodicity of a repeating structure. Consequently, information related to a physical property of a substance (such as terminal groups and chemical modifications) having the repeating structure can be checked more easily than where the conventional mass spectral representation is used. Hence, analysis of the substance having the repeating structure can be facilitated.

BRIEF DESCRIPTION OF THE DRAWINGS

FIG. 9 is a table indicating structures that mycolic acids are estimated to have.

DESCRIPTION OF THE PREFERRED EMBODIMENTS

The preferred embodiments of the present invention are hereinafter described in detail with reference to the drawings.

It is to be understood that embodiments described below inform the elements of the invention as delineated by the appended claims and that all the configurations described below are not always elements of the present invention.

1. Image Generating Apparatus

Figure 1:
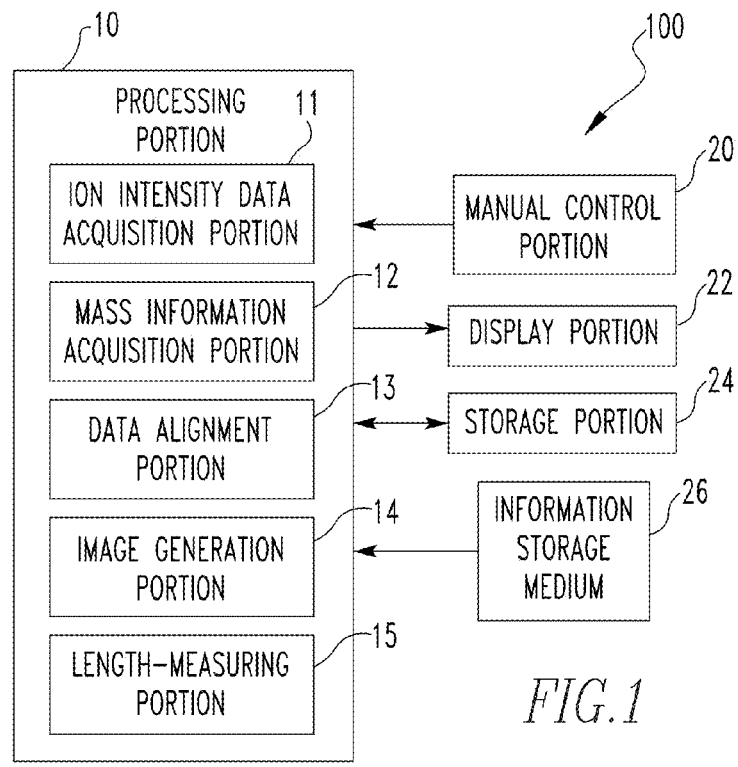
FIG. 1 is a block diagram of one example of configuration of an image generating apparatus associated with one embodiment of the present invention.

An image generating apparatus associated with one embodiment of the present invention is first described. FIG. 1 shows one example of the configuration of the image generating apparatus, generally indicated by reference numeral 100.

As shown in FIG. 1, the image generating apparatus 100 includes a processing portion 10, a manual control portion 20, a display portion 22, a storage portion 24, and an information storage medium 26. The image generating apparatus 100 can generate an image used to analyze a substance having a repeating structure.

Examples of a substance having a repeating structure include lipids and polymers. Such a substance may be referred to as the substance of interest. Generally, a lipid is an ester of an aliphatic acid and an alcohol and has a repeating structure of $CH_2$ (methylene group). A polymer is obtained by polymerization of monomer molecules and has a repeating structure of a monomer skeleton.

The processing portion 10 includes an ion intensity data acquisition portion 11, a mass information acquisition portion 12, a data alignment portion 13, and an image generation portion 14. The processing portion 10 can further include a length-measuring portion 15 (not shown). The functions of the processing portion 10 can be realized in hardware (such as various processors (e.g., CPU, DSP, or the like), ASIC (gate array or the like)) or in software.

The ion intensity data acquisition portion 11 obtains ion intensity data about the substance of interest, the data including information about a relative intensity of each ion against mass-to-charge ratio. The ion intensity data includes information about the ion intensity detected at each mass-to-charge ratio in mass analysis. Mass-to-charge ratios contained in the ion intensity data are plotted on the horizontal axis of a graph, while ion intensities are plotted on the vertical axis. Thus, a mass spectrum is obtained. The ion intensity data can be obtained, for example, from a mass spectrum, in which mass-to-charge ratio (m/z) (where m is a molecular mass and z is a valence number) is plotted on the horizontal axis, while ion intensity (relative intensity) is on the vertical axis.

Ion intensity data (i.e., a mass spectrum) about a substance of interest is obtained, for example, by making a measurement on the substance of interest by a mass spectrometer, which can be, for example, a MALDI TOF (matrix assisted laser desorption/ionization time-of-flight) mass spectrometer.

The ion intensity data acquisition portion 11 obtains ion intensity data, for example, by reading ion intensity data (mass spectral data) from the information storage medium 26. The ion intensity data acquisition portion 11 may obtain ion intensity data from only within an m/z range in which ion peaks reflecting a repeating structure appear.

The mass information acquisition portion 12 obtains mass information about the repeating unit of the substance of interest. In a case where the substance of interest is a lipid, mass information about the repeating unit is, for example, an accurate mass 14.0157u of $CH_2$ (unified atomic mass unit). The mass information acquisition portion 12 may obtain mass information about a repeating structure by permitting a user to manipulate the manual control portion 20 to enter mass information about the repeating unit and thus the manual control portion 20 outputs the entered mass information about the repeating unit to the mass information acquisition portion 12. Alternatively, the mass information acquisition portion 12 may acquire mass information related to the repeating unit of the substance of interest by previously reading mass information about the repeating unit from the information storage medium 26.

The data alignment portion 13 aligns the ion intensity data within each given range of mass-to-charge ratios based on the mass information about the repeating unit obtained by the mass information acquisition portion 12. For instance, the data alignment portion 13 aligns ion intensity data within each given range of mass-to-charge ratios along a first axis to form unit data strings and aligns the data strings along a second axis intersecting the first axis. The given range of mass-to-charge ratios corresponds, for example, to the mass of the repeating unit.

The image generation portion 14 generates an image based on the aligned ion intensity data. The image generation portion 14 can generate a two-dimensional image in which the first axis is taken as the X-axis, the second axis is taken as the Y-axis, and ion intensities indicated by the ion intensity data represent color shades.

The image generation portion 14 can generate a three-dimensional image in which the first axis is taken as the X-axis, the second axis is taken as the Y-axis, and ion intensities indicated by the ion intensity data are plotted on the Z-axis. In the case of a three-dimensional image, the image generation portion 14 may represent ion intensities in terms of both the Z-axis and color variations.

Furthermore, the image generation portion 14 can generate both a two-dimensional image and a three-dimensional image. In addition, the image generation portion 14 can arbitrarily switch the generated image between a two-dimensional image and a three-dimensional image. This clarifies the relationship between the two- and three-dimensional images, thus facilitating the analysis. Further, the image generation portion 14 can enlarge or reduce a part of the generated image. Additionally, the image generation portion 14 can create a three-dimensional image taken from various points of view. Still further, the image generation portion 14 can generate an image taken from various points of view, and can create an animation sequence that varies from two-dimensional images to three-dimensional images.

The length-measuring portion 15 can measure the distance between two points in an image, the points being specified using the manual control portion 20. Furthermore, the length-measuring portion 15 can measure the distance between two specified points in an image, the points being taken along the X-axis.

The manual control portion 20 is used by a user to enter information about manipulations. The manual control portion 20 outputs the entered information about manipulations to the processing portion 10. The functions of the manual control portion 20 can be realized by hardware such as a keyboard, a mouse, or a touch panel display. The manual control portion 20 permits one to specify a position in an image generated by the image generation portion 14. The manual control portion 20 outputs information about the specified position to the length-measuring portion 15 of the processing portion 10.

The display portion 22 is used to display the image generated by the processing portion 10. The function of the display portion can be realized by an LCD, a CRT, or the like. The display portion 22 can display the image generated by the image generation portion 14. Furthermore, the display portion 22 can display a mass spectrum.

The storage portion 24 acts as the working area of the processing portion 10 and the function of the storage portion can be realized by a RAM or the like. The information storage medium 26 that is a computer-readable medium stores computer programs and data. The functions of the medium 26 can be realized by an optical disk (CD or DVD), magnetooptical disk (MO), magnetic disk, hard disk, or memory (ROM). The processing portion 10 performs various kinds of processing of the present embodiment based on a program stored on the information storage medium 26. A program for causing a computer to function as various portions of the processing portion 10 can be stored on the information storage medium 26. This program can be installed in the information storage medium 26 from CD or DVD. This program can also be downloaded from the storage device of a server via a network such as the internet and installed in the information storage medium 26.

2. Image Generation Method

Figure 2:
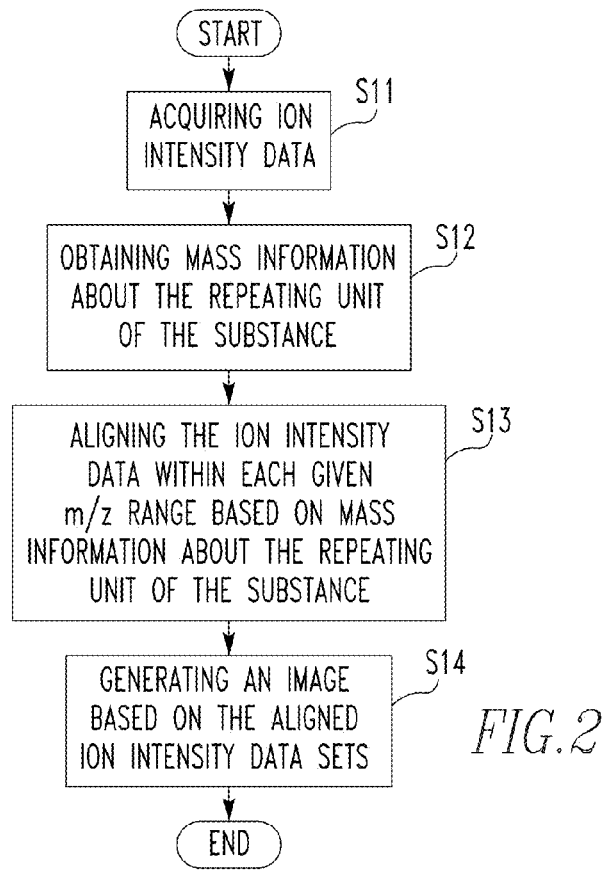
FIG. 2 is a flowchart illustrating one example of an image generation method associated with one embodiment of the invention.

An image generation method according to one embodiment of the present invention is next described. This method can be implemented using an image generating apparatus according to an embodiment of the invention. FIG. 2 is a flowchart illustrating one example of this image generation method.

(1) First, the ion intensity data acquisition portion 11 acquires ion intensity data about the substance of interest, the data including information about a relative intensity of each ion against mass-to-charge ratio (ion intensity data acquisition step S11).

Figure 3:
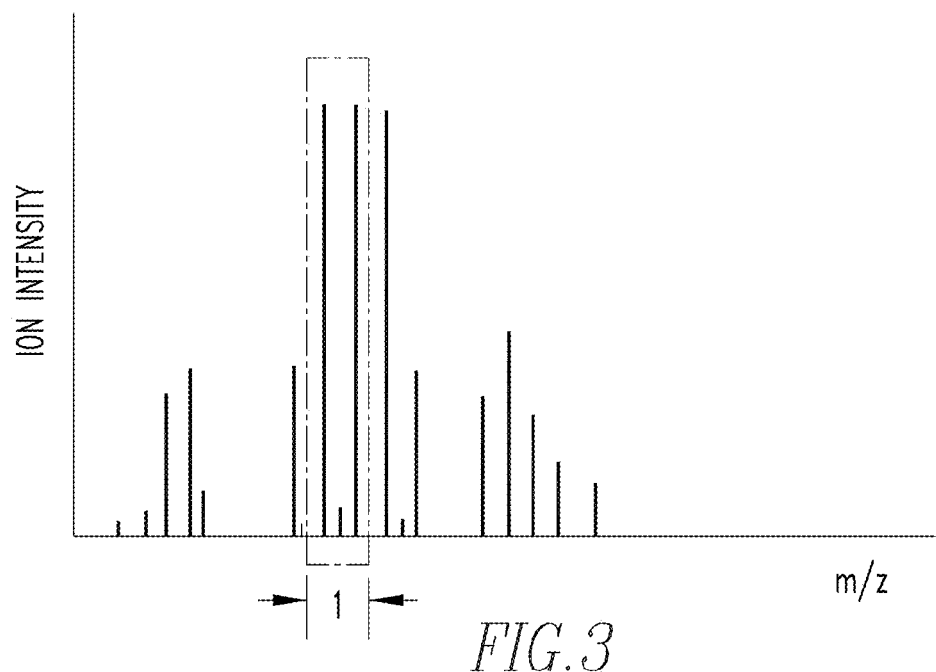
FIG. 3 is a graph illustrating an ion intensity data acquisition step.

FIG. 3 illustrates the ion intensity data acquisition step S11 and shows one example of mass spectrum of the substance of interest.

In the present step, the user specifies an m/z range 1 in which ion peaks reflecting the repeating structure of the substance of interest appear as shown in FIG. 3. In particular, the processing portion 10 displays a mass spectrum of the substance of interest on the display portion 22 based on the ion intensity data (mass spectral data) about the substance of interest stored on the information storage medium 26. The user manipulates the manual control portion 20 to specify the m/z range 1 in which the ion peaks reflecting the repeating structure appear from the mass spectrum of the substance of interest displayed on the display portion 22.

Then, the ion intensity data acquisition portion 11 acquires ion intensity data from the specified m/z range 1 by reading ion intensity data corresponding to the m/z range 1 from the information storage medium 26.

The ion intensity data acquisition portion 11 may acquire all the ion intensity data stored on the information storage medium 26 without performing the step of specifying the m/z range 1.

(2) Then, the mass information acquisition portion 12 obtains mass information about the repeating unit of the substance of interest (mass information acquisition step S12).

The mass information acquisition portion 12 then can obtain mass information about the repeating unit of the substance of interest, for example, when mass information is entered by the user through the manual control portion 20. A list, for example, in which substances and masses of repeating units of the substances are associated with each other may be previously stored on the information storage medium 26. When a user selects a substance name from the list, mass information about the repeating unit of the selected substance is output to the mass information acquisition portion 12. The acquisition portion 12 can obtain the information about the repeating unit of the substance of interest.

An accurate mass of the repeating unit of the substance of interest can be used as the mass of the repeating unit of the substance of interest. For example, where the substance of interest is a lipid, mass information about the repeating unit is an accurate mass 14.0157u of $CH_2$ (methylene group). The information about the repeating unit of the substance of interest may be a multiple (e.g., twice) of the mass of the repeating unit of the substance of interest.

(3) The data alignment portion 13 aligns the ion intensity data within each given m/z range based on mass information about the repeating unit of the substance of interest obtained by the mass information acquisition portion 12 (data alignment step S13).

Figure 4:
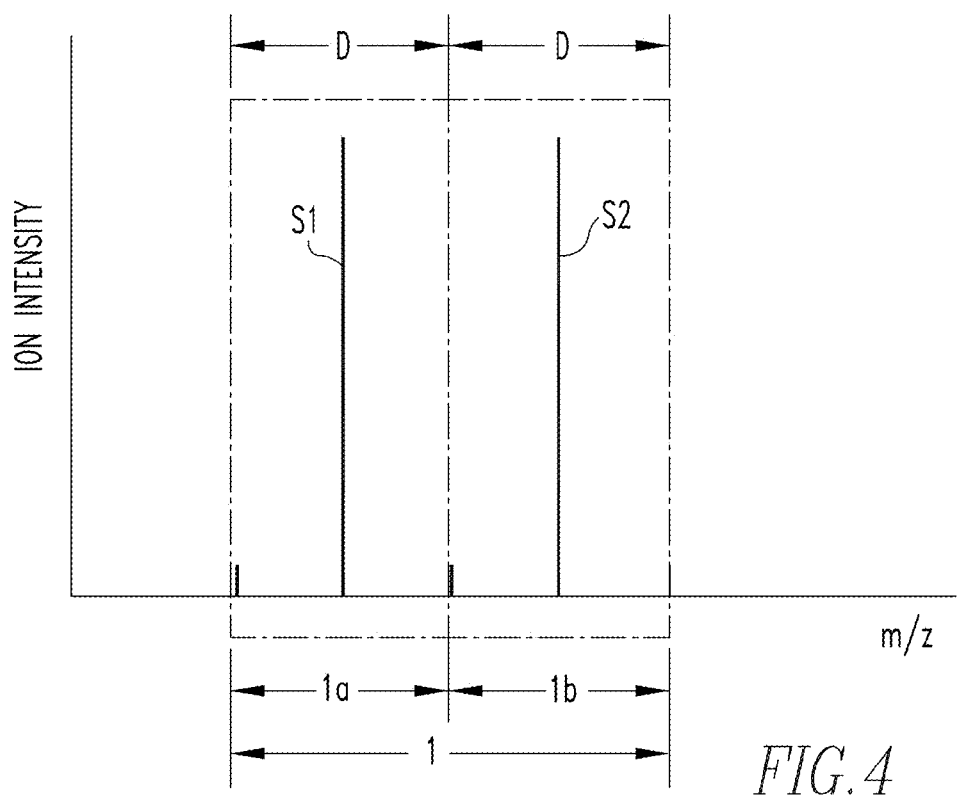
FIG. 4 is a graph illustrating a data alignment step.
Figure 5A:
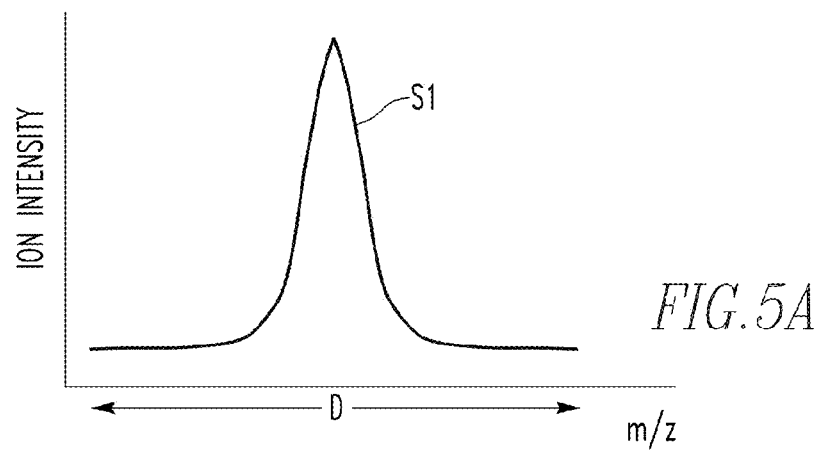
FIGS. 5A and 5B are graphs illustrating a data alignment step.
Figure 5B:
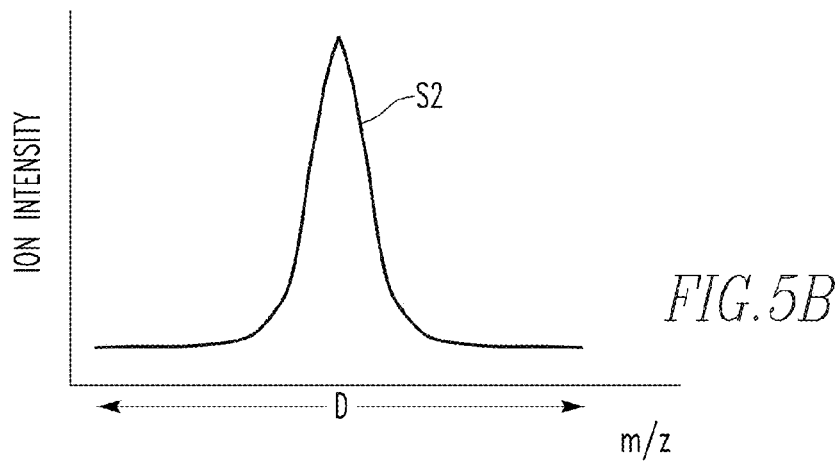
Figure 6:
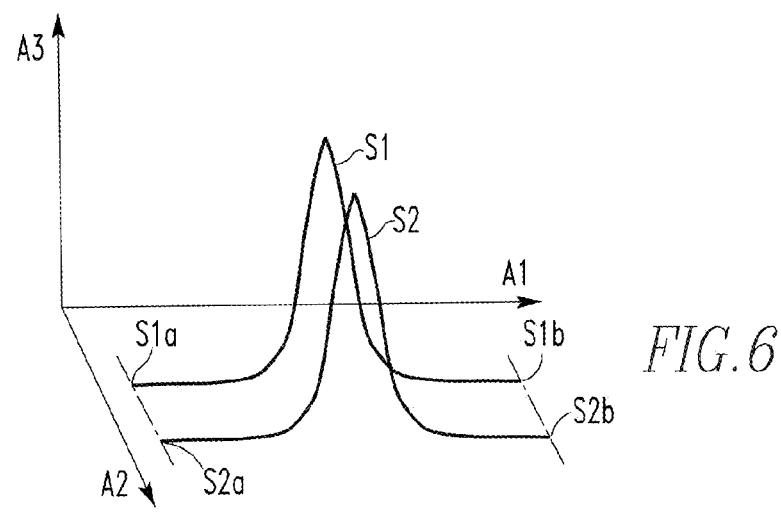
FIG. 6 is a graph illustrating another data alignment step.

FIGS. 4-6 illustrate the data alignment step S13. FIG. 4 is an enlarged view of the range 1 shown in FIG. 3. FIG. 5A is an enlarged view of the ion intensity data set (mass spectrum S1) in an m/z range 1a shown in FIG. 4. FIG. 5B is an enlarged view of the ion intensity data set (mass spectrum S2) in an m/z range 1b shown in FIG. 4. In FIG. 6, the ion intensity data set (mass spectrum S1) shown in FIG. 5A and the ion intensity data set (mass spectrum S2) shown in FIG. 5B are aligned. In the data alignment step S13 described below, the data alignment portion 13 performs processing based on ion intensity data. In FIGS. 4-6, ion intensity data is shown as a mass spectrum to visually grasp the ion intensity data.

Specifically, in the present step, the data alignment portion 13 sets a range D of mass-to-charge ratios from information about the repeating unit of the substance of interest as shown in FIG. 4. In the example of FIG. 4, the range D of mass-to-charge ratios corresponds to the mass of the repeating unit of the substance of interest. That is, where the substance of interest is a lipid, the range D of the mass-to-charge ratios is an accurate mass 14.0157u of $CH_2$ (methylene group). The range D of the mass-to-charge ratios may be a multiple (e.g., twice) of the mass of the repeating unit of the substance of interest in an unillustrated manner.

Then, the data alignment portion 13 divides ion intensity data within each range D of mass-to-charge ratios. In the example of FIG. 4, the data alignment portion 13 divides ion intensity data (mass spectrum) into ion intensity data (mass spectrum S1) arising from the range 1a of m/z ratios and intensity data (mass spectrum S2) arising from the range 1b of m/z ratios within each range D of m/z ratios. The ion intensity data may be divided into any arbitrary number as long as it is two or greater. The data alignment portion 13 can obtain a set of ion intensity data (mass spectrum S1) arising from the range 1a shown in FIG. 5A and a set of ion intensity data (mass spectrum S2) arising from the range 1b shown in FIG. 5B.

As shown in FIG. 6, the data alignment portion 13 then aligns the ion intensity data (mass spectrum S1) and the ion intensity data (mass spectrum S2). In particular, the data alignment portion 13 aligns the ion intensity data (mass spectrum S1) arising from the range 1a and the ion intensity data (mass spectrum S2) arising from the range 1b along an axis A1 to form unit data strings, and aligns the unit data strings (mass spectra S1 and S2) along an axis A2 intersecting with the axis A1. For example, the axes A1 and A2 are perpendicular to each other. The data alignment portion 13 aligns the unit data strings (mass spectra S1 and S2) according to mass-to-charge ratio. More specifically, the alignment portion 13 compares the mass-to-charge ratio, for example, at the starting point S1a of the ion intensity data (mass spectrum S1) arising from the range 1a and the mass-to-charge ratio at the starting point S2a of the ion intensity data (mass spectrum S2) arising from the range 1b and aligns the values in turn from the lowest value (in the illustrated example, from the mass spectrum S1) along the axis A2.

In the example of FIG. 6, the data alignment portion 13 aligns the starting point S1a of the ion intensity data (mass spectrum S1) arising from the range 1a and the starting point S2a of the ion intensity data (mass spectrum S2) arising from the range 1b along the axis A2, i.e., they are at the same coordinate on the axis A1. Similarly, the data alignment portion 13 aligns the ending point S1b of the ion intensity data (mass spectrum S1) arising from the range 1a and the ending point S2b of the ion intensity data (mass spectrum S2) arising from the range 1b along the axis A2, i.e., at the same coordinate on the axis A1. In the example of FIG. 6, an axis A3 indicates ion intensities indicated by ion intensity data. For example, the axis A3 is perpendicular to both axes A1 and A2.

(4) Then, the image generation portion 14 generates an image based on the aligned ion intensity data sets (mass spectra S1 and S2) (image generation step S14).

Figure 7:
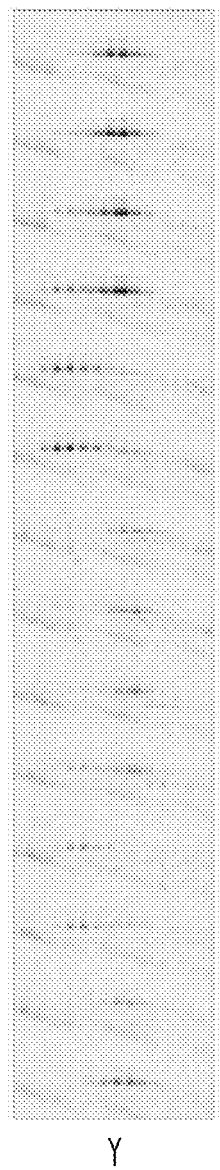
FIG. 7 shows one example of image generated by an image generation portion.
Figure 8:
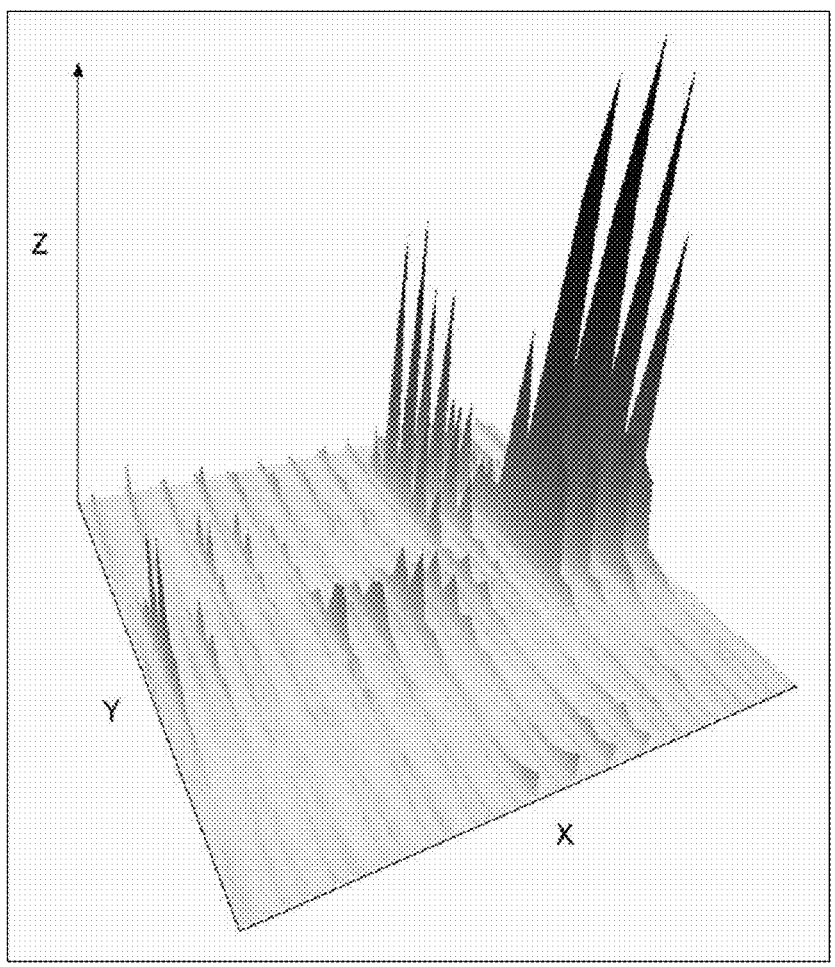
FIG. 8 shows one example of image generated by an image generation portion.

FIGS. 7 and 8 are charts showing examples generated by the image generation portion 14. In the description of the above example shown in FIGS. 3-6, ion intensity data are aligned as two rows. In FIGS. 7 and 8, an example in which ion intensity data are arrayed as 30 rows to form an image.

As shown in FIG. 7, the image generation portion 14 generates a two-dimensional image in which axis A1 is taken as the X-axis, axis A2 is taken as the Y-axis, and axis A3 represents color shades. Furthermore, as shown in FIG. 8, the image generation portion 14 creates a three-dimensional image in which axis A1 is taken as the X-axis, axis A2 is taken as the Y-axis, and axis A3 is taken as the Z-axis. The image generation portion 14 generates a three-dimensional image, for example, by dividing the ion intensity data as aligned as shown in FIG. 6 into triangles and creating links between data points.

In this way, the image generation portion 14 can generate an image whose X-axis corresponds to mass-to-charge ratio and whose Y-axis corresponds to the period of a repeating structure by creating the image in which axes A1 and A2 are taken as the X-axis and the Y-axis, respectively. The period of the repeating structure can be made to correspond to the number of repeating units or to the degree of overlap.

For example, the image generation portion 14 generates a two-dimensional image having ion peaks whose positions (X- and Y-coordinates) can be easily confirmed. That is, the image generation portion creates a two-dimensional image permitting one to easily check to what row and to what column does an ion peak of interest belong on the image. In particular, regions (in the illustrated example, rectangular regions) are assigned to corresponding coordinates. A shade of color corresponding to an ion intensity is given to each region. Consequently, the positions (coordinates) of ion peaks can be clarified. In this two-dimensional image, deviations of ion peaks, period, spacing between ion peaks, and so on can be easily checked.

The image generation portion 14 generates a three-dimensional image in which ion peaks are connected together smoothly. In particular, adjacent ion peaks are smoothly connected together by performing interpolation between the adjacent ion peaks. In this three-dimensional image, the ion peak intensity distribution (intensity variations) can be grasped easily.

Then, the image generated by the image generation portion 14 is displayed on the display portion 22. The image generated by the image generation portion 14 may be output to a recording medium such as paper.

Because of these steps, an image for analyzing a substance having a repeating structure can be generated.

3. Examples

The present embodiment is described in further detail below by taking its examples. It is to be understood that the present invention is not limited thereby.

3.1. Example 1

(1) Sample

Mycolic acid that is one type of fatty acid and found in Mycobacterium tuberculosis was used as a sample (substance of interest). FIG. 9 is a table showing structures that mycolic acids are estimated to have. The mycolic acids were measured by MALDI TOF MS and mass spectra were obtained.

Figure 10:
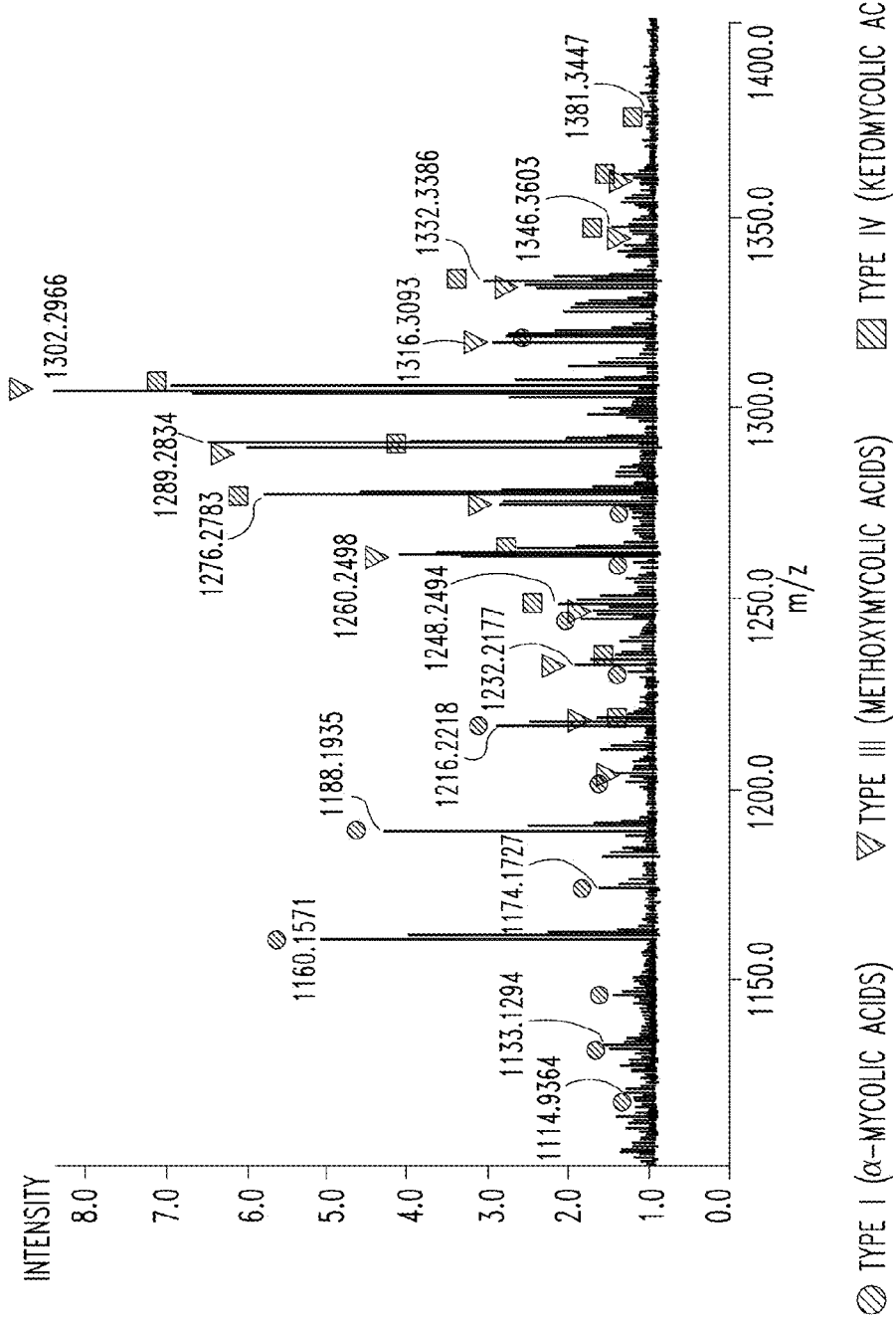
FIG. 10 is a graph showing a mass spectrum of mycolic acids.

FIG. 10 is a graph showing a mass spectrum of mycolic acids.

(2) Image Generation Conditions

The accurate mass 14.0157u of the repeating unit $CH_2$ (methylene group) of the fatty acid was used as the mass of the repeating unit. The imaged range 1 of mass-to-charge ratios was set from 1067.6037 to 1503.0889. The number of data points in the ion intensity data was 106309.

(3) Results

Figure 11:
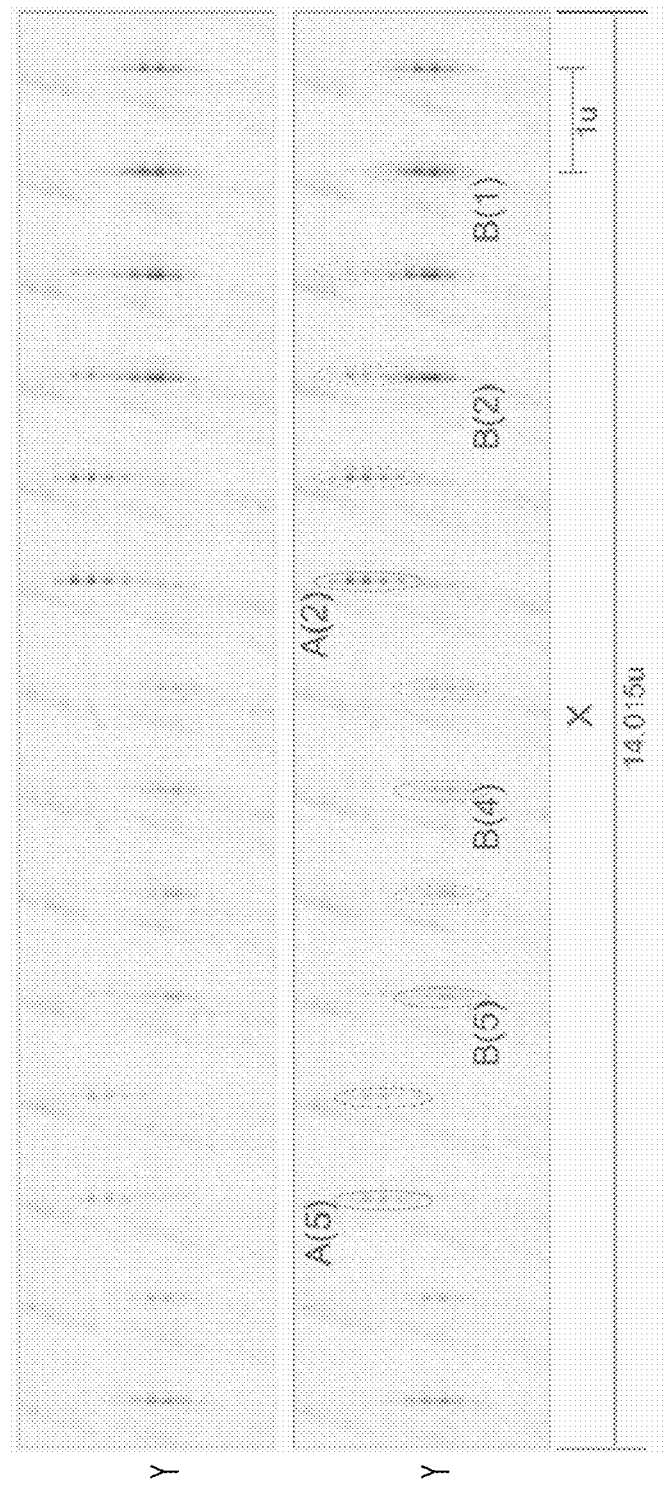
FIG. 11 is an image generated using an image generating apparatus associated with one embodiment of the present invention from a mass spectrum of mycolic acids.
Figure 12:
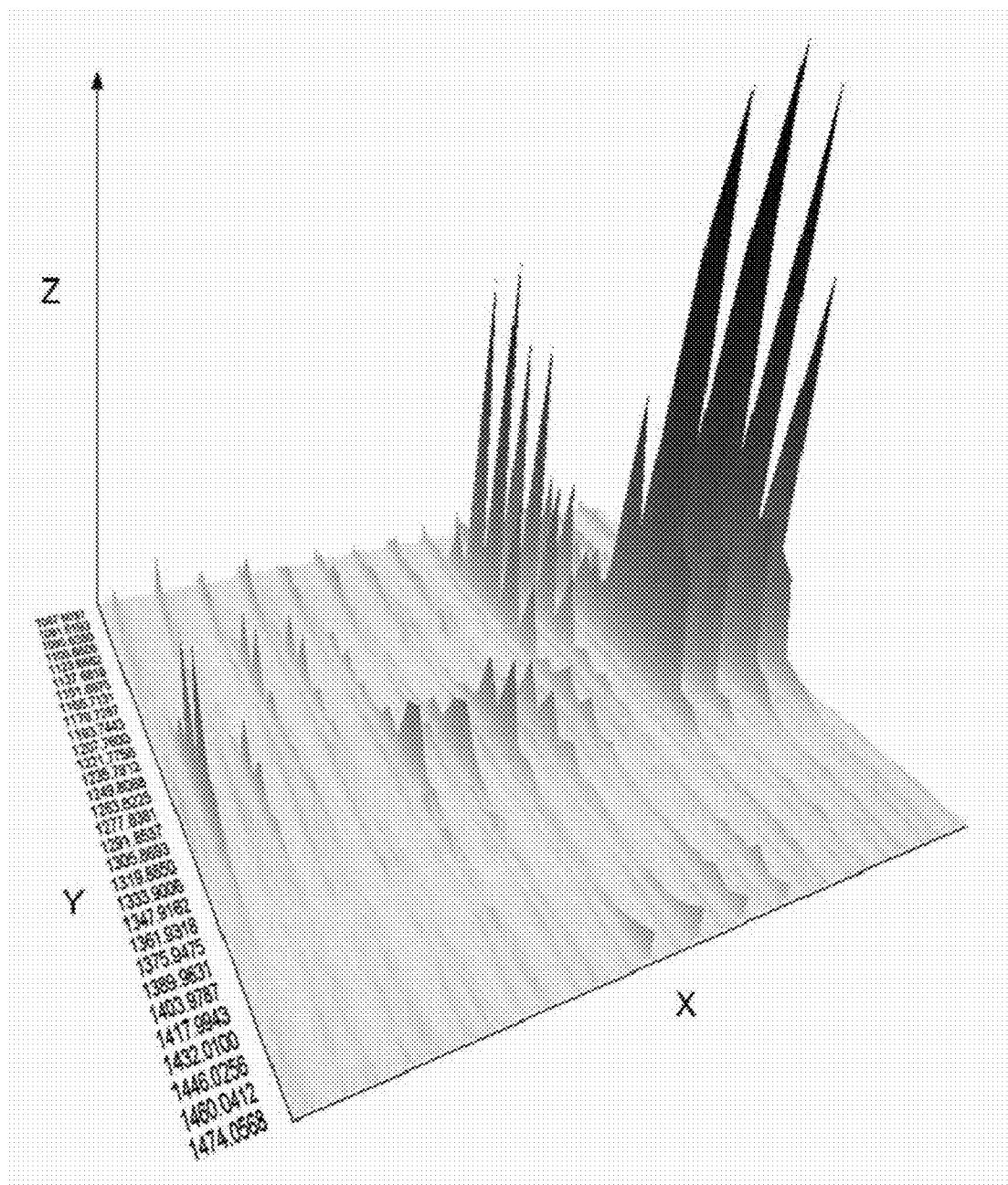
FIG. 12 is an image generated using an image generating apparatus according to the invention from a mass spectrum of mycolic acids.

FIG. 11 is a two-dimensional image generated from a mass spectrum of mycolic acids shown in FIG. 10 by the use of the image generating apparatus associated with the present embodiment. FIG. 12 is a three-dimensional image generated from the mass spectrum of mycolic acids shown in FIG. 10 through the use of the image generating apparatus associated with the present embodiment. In FIGS. 11 and 12, ion intensities are indicated by color shades. As the color gets denser, the ion intensity increases. In FIG. 11, portions indicated by dotted lines indicate isotopes.

It can be easily seen from the images shown in FIGS. 11 and 12 that plural ion peaks are arrayed along the Y-axis because of the repeating structure of $CH_2$. Furthermore, the phenomenon that alternate ion peaks of the repeating structure are increased in intensity, as reported by F. Laval, M. A. Lanéelle, C. Déon, B. Monsarrat, and M. Daffé, Accurate molecular mass determination of mycolic acids by MALDI-TOF mass spectrometry. Analytical Chemistry, 73 (18): 4537-4544, 2001 can be checked easily.

In addition, information about terminal groups can be obtained from the image shown in FIG. 11. Where the hydrocarbons in terminal groups have double bonds, the mass is reduced by an amount corresponding to two hydrogen atoms, i.e., 2u. That is, in the image shown in FIG. 11, the difference $2u$ in the X-axis direction indicates a difference in number between double bonds. It can be confirmed from the image shown in FIG. 11 that this difference occurs between B(1) and B(2) and between B(4) and B(5).

In this way, in the image shown in FIG. 11, differences between terminal groups of lipids are visualized, and information about the terminal groups can be easily confirmed.

Furthermore, where one wants to check at what position within a molecule a chemical modification is made, a pure substance and an MS/MS mass spectrum are needed. An analysis can be performed similarly by the present technique.

3.2. Example 2

The present technique was employed as a method of checking the calibration of mass-to-charge ratios in a mass spectrometer.

(1) Sample

A sample which is a known substance and whose ion peaks are known was used for calibration. In this example, PMMA (polymethyl methacrylate) was used as a sample.

The PMMA was measured by MALDI TOF MS in the condition where the calibration of mass-to-charge ratios was appropriate, and a mass spectrum of the PMMA was obtained.

Figure 13:
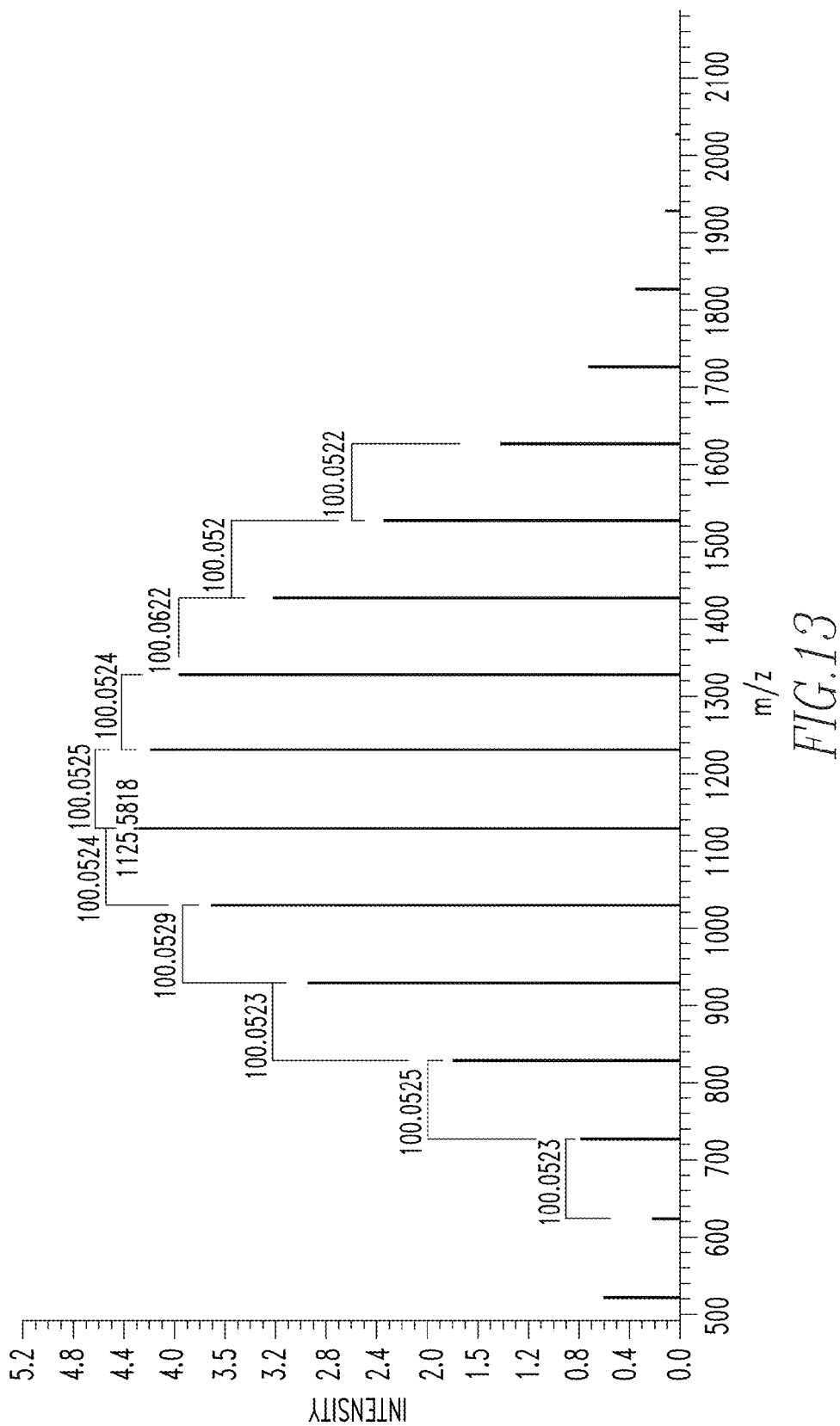
FIG. 13 is a graph showing a mass spectrum of PMMA obtained under the condition where calibration of mass-to-charge ratios is appropriate.

FIG. 13 is a graph showing a mass spectrum of PMMA measured under the condition where the calibration of mass-to-charge ratios was appropriate.

Then, PMMA was measured by MALDI TOF MS in the condition where the calibration of mass-to-charge ratios was inappropriate, and a mass spectrum of the PMMA was obtained.

(2) Image Generation Conditions

An accurate mass 100.05243u of the repeating unit $^{12}C_5{}^{1}H_8{}^{16}O_2$ (methylmethacrylate skeleton that is a monomer skeleton) of PMMA (polymethyl methacrylate resin) was used as the mass of the repeating unit.

(3) Results

Figure 14:
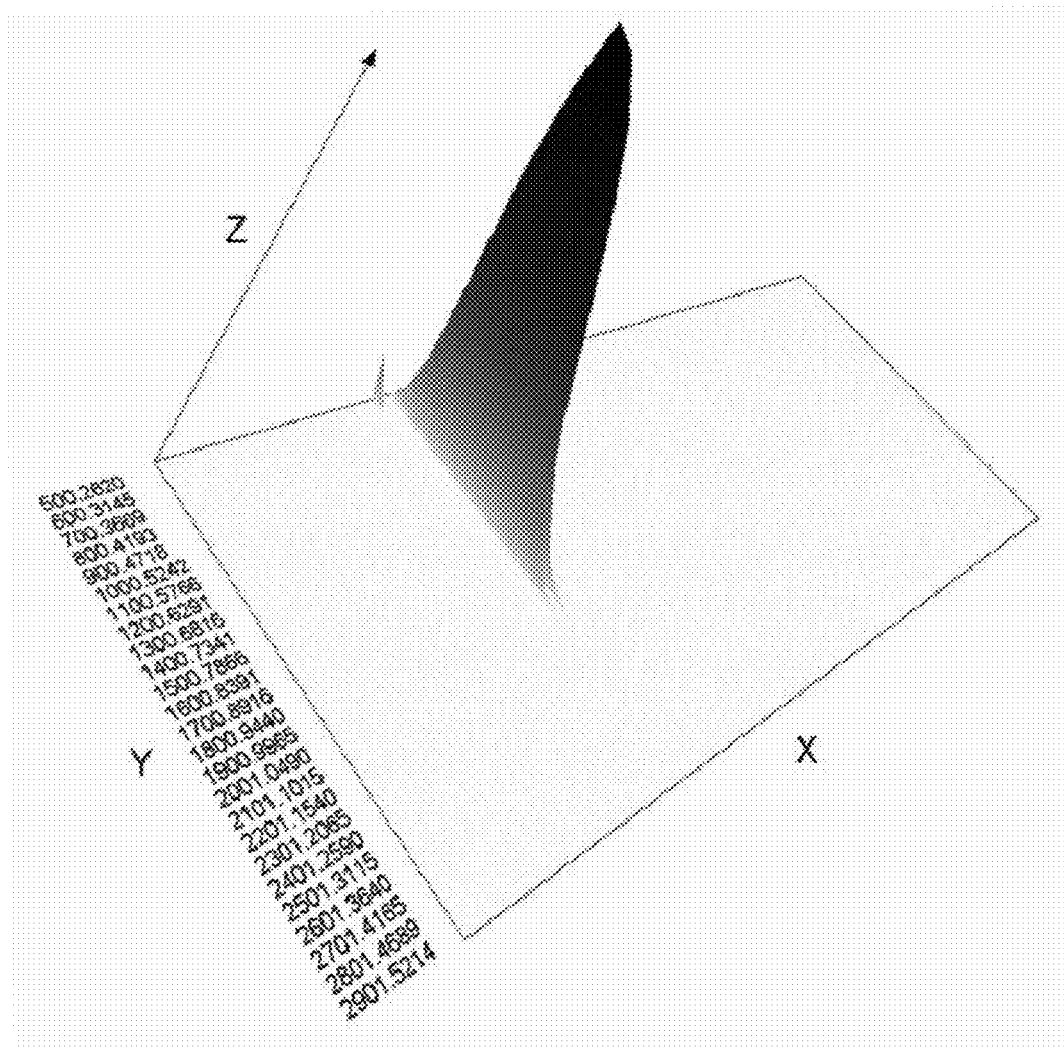
FIG. 14 is a three-dimensional image generated from a mass spectrum of PMMA obtained under the condition where calibration of mass-to-charge ratios is appropriate.
Figure 15:
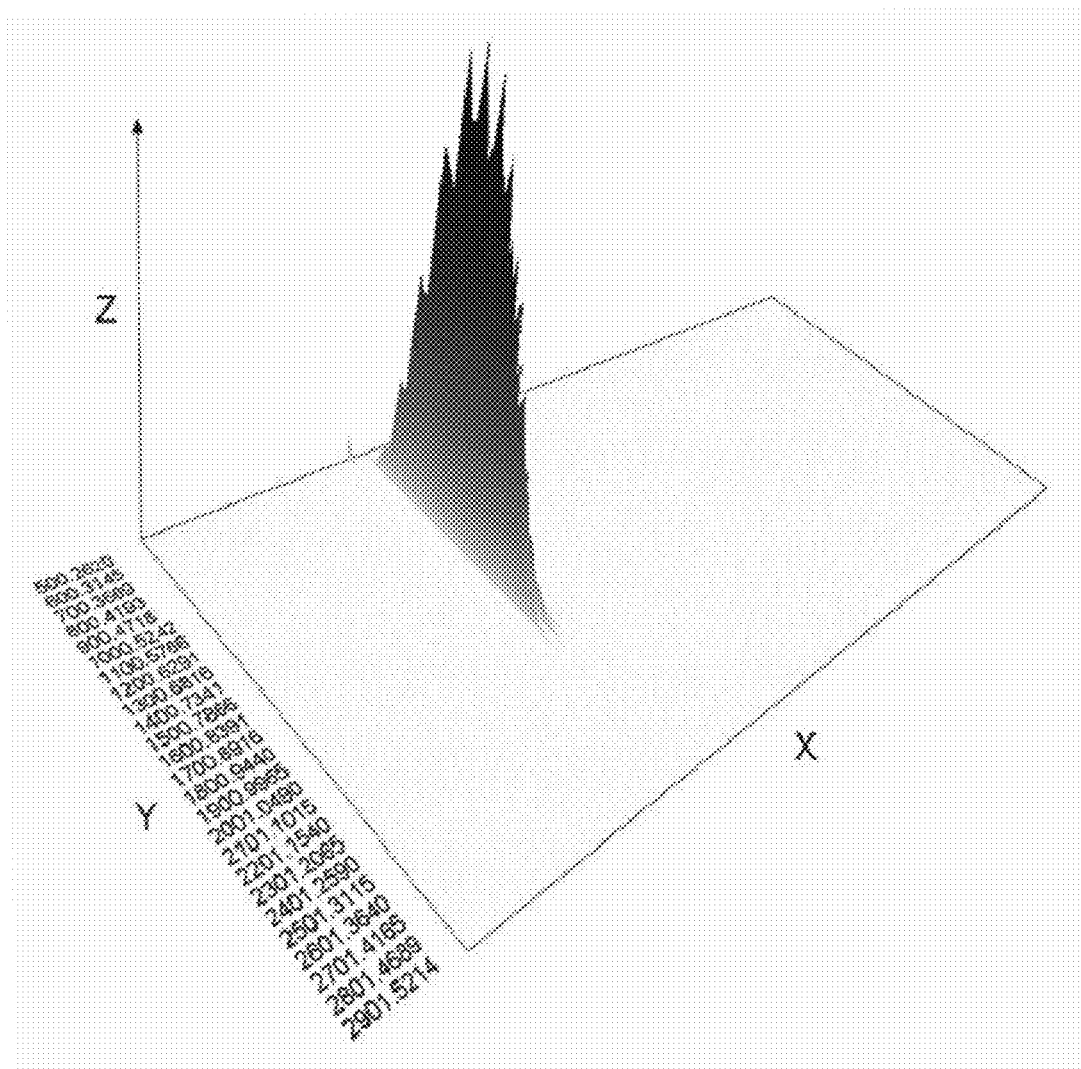
FIG. 15 is a three-dimensional image generated from a mass spectrum of PMMA obtained under the condition where calibration of mass-to-charge ratios is inappropriate.

FIG. 14 is a three-dimensional image created using the image generating apparatus associated with the present embodiment from the mass spectrum (shown in FIG. 13) of PMMA in a case where a measurement was made under the condition where the calibration of mass-to-charge ratios was appropriate. FIG. 15 is a three-dimensional image created using the image generating apparatus associated with the present embodiment from the mass spectrum of PMMA in a case where a measurement was made under the condition where the calibration of mass-to-charge ratios was inappropriate.

As shown in FIG. 14, in a case where the calibration of mass-to-charge ratios is appropriate, it can be confirmed that ion peaks arising from PMMA are aligned along the Y-axis in the generated three-dimensional image. It can be checked that the ion peaks arising from PMMA are smoothly interconnected like a curve along the Y-axis. However, as shown in FIG. 15, in a case where the calibration of mass-to-charge ratios is inappropriate, it can be confirmed that ion peaks arising from PMMA are connected together not smoothly but convexly and concavely in the obtained three-dimensional image. Such convex and concave geometries appeared because peaks of ions having a repeating unit of one less or more value did not appear in the adjacent vertices of the triangular sections when adjacent ion peaks were interconnected. That is, the convex and concave geometries appeared while reflecting deviations of the calibration of mass-to-charge ratios.

It is easy to check whether calibration of a mass spectrometer in terms of mass-to-charge ratios is appropriate by generating a three-dimensional image by the use of an image generating apparatus associated with the present embodiment.

In the present embodiment, ion data intensity data are aligned within each given range of mass-to-charge ratios based on mass information about the repeating unit of the substance of interest. An image is generated based on the aligned ion intensity data. Consequently, it is possible to obtain an image in which ion intensities are expanded not only along the m/z axis (along the X-axis in FIGS. 7 and 8) but also along the axis of periodicity of a repeating structure (along the Y-axis in FIGS. 7 and 8).

In the conventional mass spectral representation, ion intensities have been expanded along the m/z axis. In contrast, in the present embodiment, it is possible to obtain an image in which ion intensities are expanded not only along the m/z axis but also along the axis of periodicity of a repeating structure as described previously. In consequence, the display space can be used efficiently, and a large amount of information can be displayed efficiently. For this reason, various kinds of important information such as repeating unit, ion intensity distribution, terminal groups, chemical modifications, and so on associated with physical properties of a substance having a repeating structure can be confirmed more easily than where the conventional mass spectral representation is used. Hence, according to the present embodiment, analysis of the substance having the repeating structure can be facilitated.

Furthermore, in the conventional mass spectral representation, ion peaks arising, for example, from a repeating structure must be assigned one by one. In contrast, in an image where ion intensities are expanded along the m/z axis and along the axis of periodicity of a repeating structure, ion peaks arising from a substance, for example, having the same terminal group are arrayed along the Y-axis. Therefore, ion peaks aligned along the Y-axis can be assigned at once. Consequently, the analysis time can be shortened compared with the conventional mass spectral representation. According to the present embodiment, an image capable of providing a shorter analysis time can be generated compared with the prior art mass spectral representation.

Furthermore, in an image in which ion intensities are expanded along the m/z axis and along the axis of periodicity of a repeating structure, ion peaks having a period corresponding to the unit mass of the repeating structure are aligned in a line along the Y-axis. For example, in the two-dimensional image shown in FIG. 11, ion peaks of a substance having the same terminal group are aligned in a line along the Y-axis. Accordingly, with this image, deviations of ion peaks and periodicity can be checked more easily than with the conventional mass spectral representation. Since a straight line is detected by a one-dimensional visual area, high-speed recognition is possible in human visual information processing. Therefore, ion peaks aligned in a line can be recognized even from among noises at high speed.

In an image where ion intensities are expanded along the m/z axis and along the axis of periodicity of a repeating structure, ion peaks, for example, of isotopes are aligned along an axis (e.g., Y-axis). In a mass spectrum, ion peaks of isotopes appear. Such ion peaks of isotopes can be used as information for enhancing the accuracy of analysis. However, the ion peaks of isotopes complicate mass spectra. In some cases, analysis is made difficult to perform in the case of the conventional mass spectral representation. In an image where ion intensities are expanded along the m/z axis and along the axis of periodicity of a repeating structure, ion peaks of isotopes are aligned along an axis and so analysis is performed more easily than with the conventional mass spectral representation. The accuracy of analysis can be enhanced.

According to the present embodiment, it is possible to generate a two-dimensional image in which axis A1 is taken as the X-axis, axis A2 is taken as the Y-axis, and ion intensities indicated by ion intensity data give color shades. Consequently, it is possible to generate an image permitting one to easily check deviations of ion peaks, period, spacing between ion peaks, and other information. The lipid used as a sample in Examples 1 and 2 of the present embodiment is often analyzed in the field of biology. In electrophoresis employing electrophoretic gel used in the field of biology, it is common practice to represent intensities in terms of color shades. Therefore, the aforementioned two-dimensional image is similar to the method of representing results of electrophoretic measurements. Accordingly, in a case where a lipid is analyzed, for example, the two-dimensional image resembles images that biologic users often encounter. This can promote analysis performed by the users.

According to the present embodiment, it is possible to generate a three-dimensional image in which axis A1 is taken as the X-axis, axis A2 is taken as the Y-axis, and ion intensities indicated by ion intensity data are plotted on the Z-axis. Consequently, an image permitting one to easily grasp variations in ion intensity or distribution or other similar information can be created.

According to the present embodiment, both a two-dimensional image (see FIG. 7) and a three-dimensional image (see FIG. 8) can be generated as described previously. In the two-dimensional image, ion intensities are represented in terms of color variations. Therefore, in some cases, it is difficult to confirm ion intensity variations. In contrast, in the three-dimensional image, ion intensities are represented by the Z-axis and, therefore, variations in ion intensity can be checked easily. Furthermore, in a three-dimensional image, deviations of ion peaks, period, and spacing between ion peaks may not be easily confirmed. In addition, adjacent layers overlap, creating the problem of occlusion. In contrast, in a two-dimensional image, deviations of ion peaks, period, and spacing between ion peaks can be checked easily. Also, the problem of occlusion does not take place. By generating both a two-dimensional image and a three-dimensional image in this way, analysis can be facilitated.

According to the present embodiment, the distance between two points in a generated image taken along the X-axis can be measured. This makes it easy to check the difference in mass-to-charge ratio between peaks. Consequently, terminal groups and chemical modifications can be easily analyzed.

It is to be understood that the above-described embodiment merely constitutes one example of the invention and that the invention is not restricted thereby.

For example, in the above embodiment, an example in which a MALDI TOF mass spectrometer is used as a mass spectrometer is taken. The present invention can be applied irrespective of the combination of preprocessing and an ionization method if a repeating structure appears in the mass spectrum.

The present invention embraces configurations (such as configurations identical in function, method, and results or configurations identical in purpose and advantageous effects) substantially identical with the configurations described in the embodiment. Furthermore, the invention embraces configurations which are similar to the configurations described in the above embodiment except that nonessential parts thereof have been replaced. In addition, the invention embraces configurations identical in advantageous effects or purpose with the configurations described in the above embodiment. Further, the invention embraces configurations which are similar to the configurations of the above embodiment except that well-known techniques are added.

Having thus described our invention with the detail and particularity required by the Patent Laws, what is desired protected by Letters Patent is set forth in the following claims.

The invention claimed is:

1. An image generating apparatus for generating a two- or three-dimensional image for analyzing a substance whose mass spectrum has ion peaks at equal intervals reflecting repeating structures, said image generating apparatus comprising:

a mass spectrum data acquisition means for acquiring a combined mass spectrum arising from the substance obtained by using a mass spectrometer, the data including combined information about relative intensities of ions and respective mass-to-charge ratios;

an input device for entering a mass range (D) of the repeating structure of the substance;

a data alignment means for obtaining a series of unit data strings from the combined mass spectrum defining separate mass spectra (S1, S2 . . . Sn) corresponding to each ion of the substance by dividing the combined mass spectrum into separate spectra, each of said separate spectra having equal width of the mass range (D), and for two dimensionally aligning the said series of unit data strings along a first axis (A1) according to mass-to-charge ratio and a second axis (A2) according to the order of the unit data strings defining mass spectra (S1, S2 . . . Sn); and an image generation means for generating a two- or three-dimensional image based on the aligned unit data strings.

2. An image generating apparatus as set forth in claim 1, wherein said image generation means generates a two-dimensional image in which said first axis is taken as an X-axis, said second axis is taken as a Y-axis, and said ion intensities indicated by said ion intensity data are represented as color shades.

3. An image generating apparatus as set forth in claim 2, further comprising:

a position-specifying means permitting one to specify positions in the image generated by said image generation portion; and a length-measuring means for measuring a distance between two points along the X-axis, the two points being specified by the position-specifying portion.

4. An image generating apparatus as set forth in claim 1, wherein said image generation means generates a three-dimensional image in which said first axis is taken as an X-axis, said second axis is taken as a Y-axis, and said ion intensities indicated by said ion intensity data are plotted on a Z-axis.

5. An image generating apparatus as set forth in claim 4, further comprising:

a position-specifying means permitting one to specify positions in the image generated by said image generation means; and a length-measuring means for measuring a distance between two points along the X-axis, the two points being specified by the position-specifying portion.

6. An image generating apparatus as set forth in claim 1, wherein said repeating structure of the substance is a methylene group.

7. An image generating apparatus as set forth in claim 1, wherein said repeating structure of the substance is a monomer skeleton within a polymer molecule.

8. An image generation method for generating a two- or three-dimensional image used for analysis of a substance whose mass spectrum has ion peaks at equal intervals reflecting plural numbers of repeating structures, said method comprising the steps of:

acquiring ion intensity data about the substance obtained using a mass spectrometer, the data including a combined mass spectrum about a relative intensity of each ion of the substance against mass-to-charge ratio;

entering or setting a mass range (D) which corresponds to the mass of the repeating structure of the substance;

obtaining a series of unit data strings defining mass spectra (S1, S2 . . . Sn) corresponding to each ion of the substance by dividing the combined mass spectrum by the mass range (D) into separate spectra, each of said separate spectrum having equal width of mass range (D), and two dimensionally aligning the said series of unit data strings along a first axis (A1) according to mass-to-charge ratio and a second axis (A2) according to the order of the unit data strings defining mass spectra (S1, S2 . . . Sn); and generating a two- or three-dimensional image based on the aligned unit data strings.

9. An image generation method as set forth in claim 8, wherein said repeating structure of the substance is a methylene group.

10. An image generation method as set forth in claim 8, wherein said repeating structure of the substance is a monomer skeleton within a polymer molecule.

11. A non-transitory computer readable storage medium that stores a computer program for generating an image used to analyze a substance having plural numbers of repeating structures, said computer program operating to cause a computer to function as:

an ion intensity data acquisition program step for acquiring ion intensity data arising from the substance obtained by using a mass spectrometer, the data including a combined mass spectrum including information about a relative intensity of each ion of the substance against mass-to-charge ratio;

a mass information acquisition program step for entering a mass range (D) of the repeating structure of the substance;

a data alignment program step for obtaining a series of unit data strings from the combined mass spectrum defining mass spectra (S1, S2 . . . Sn) corresponding to each ion of the substance by dividing the combined mass spectrum into separate spectra, each of said separate spectrum having equal width by the mass range (D), and two dimensionally aligning the said series of unit data strings along a first axis (A1) according to mass-to-charge ratio and a second axis (A2) according to the order of the unit data strings defining mass spectra (S1, S2 . . . Sn); and an image generation program step for generating the image based on the aligned unit data strings.

12. A non-transitory computer readable storage medium as set forth in claim 11, wherein said repeating structure of the substance is a methylene group.

13. A non-transitory computer readable storage medium as set forth in claim 11, wherein said repeating structure of the substance is a monomer skeleton within a polymer molecule.

* * * * *